United States Patent [19]
Avalos et al.

[11] Patent Number: 6,083,508
[45] Date of Patent: Jul. 4, 2000

[54] METHOD OF PROCESSING ALOE LEAVES

[76] Inventors: Ramiro Estrada Avalos, Calle Mendez #501, Jaumave Tam, Mexico, 87930; Ivan E. Danhof, 222 SW. 2nd St., Grand Prairie, Tex. 75051

[21] Appl. No.: 09/081,408

[22] Filed: May 19, 1998

[51] Int. Cl.⁷ .......................... A01N 65/00; A61K 35/78; A61K 39/385; C07G 17/00
[52] U.S. Cl. ........................................ 424/195.1; 435/267
[58] Field of Search .......................... 424/195.1; 435/267

[56] References Cited

U.S. PATENT DOCUMENTS

| | | | |
|---|---|---|---|
| 4,178,372 | 12/1979 | Coats | 424/195.1 |
| 4,917,890 | 4/1990 | McAnalley | 424/195.1 |
| 5,356,811 | 10/1994 | Coats | 435/267 |
| 5,824,659 | 10/1998 | Strickland et al. | 514/54 |

OTHER PUBLICATIONS

Ivan E. Danhof, Ph.D., Remarkable Aloe (Aloe Through the Ages), 1967, pp. 25–34; pp. 38–67.

*Primary Examiner*—Jon P. Weber
*Assistant Examiner*—Deborah K. Ware
*Attorney, Agent, or Firm*—Jones, Day, Reavis & Pogue

[57] ABSTRACT

A process for forming an aloe product from only the leaf residue obtained after filleting aloe leaves having an internal fillet which is removed therefrom. Further, the residue is formed into a slurry by grinding and the aloe product is generated from the slurry. Hand filleting of the aloe leaves to remove the internal fillet may be performed as a preferable alternative to machine filleting. In addition the steps of preparing the aloe product comprises cleansing an aloe leaf before filleting it, separating the slurry formed into a liquid and solids, and further treating the separated liquid to remove laxatives before forming the aloe product. Also a process including all of the above steps may also be performed in order to form the liquid.

13 Claims, 5 Drawing Sheets

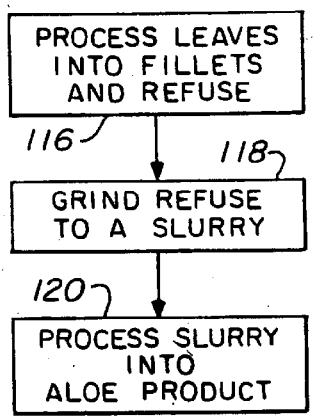
FIG. 7
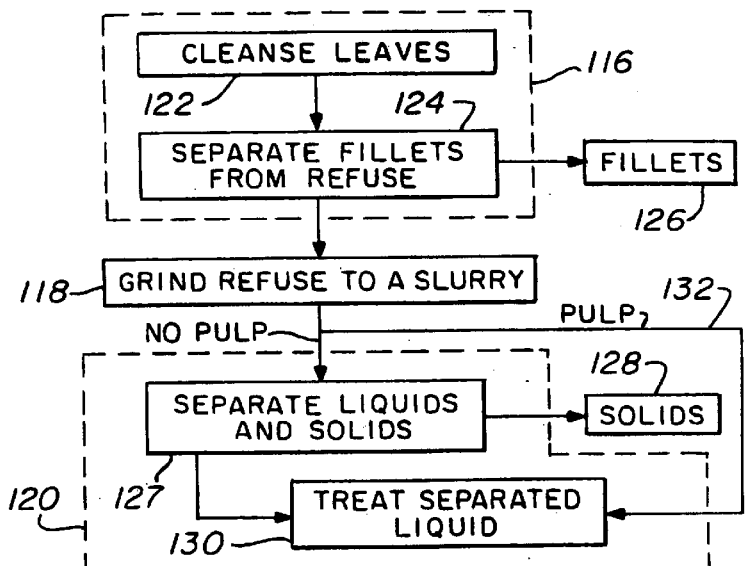
FIG. 8
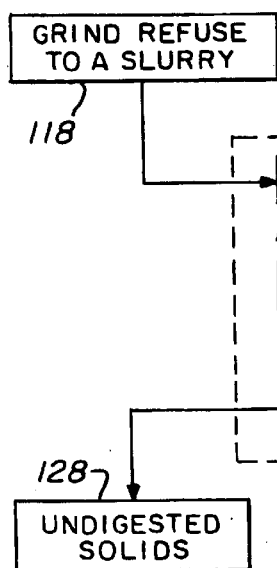
FIG. 9
| HAND-FILLETED PROCESSING | | | | | | | |
|---|---|---|---|---|---|---|---|
| LEAVES | pH | TOTAL SOLIDS (%) | MeOH SOLIDS | | | CALCIUM (mg/L) | MAGNESIUM (mg/L) |
| | | | TOTAL (%) | MALIC ACID (mg/L) | POLYSAC-CHARIDES (mg/L) | | |
| ALOE CORP | 3.77 | 0.740 (7400 mg/L) | 0.156 (1560 mg/L) | 1342 | 218 | 101 | 41.9 |
| ALOE LABS | 3.48 | 1.057 (10570 mg/L) | 0.180 (1800 mg/L) | 1284 | 516 | 208 | 44.2 |
| JAUMAVE | 4.81 | 1.203 (12030 mg/L) | 0.344 (3440 mg/L) | 1458 | 1982 | 413 | 91.0 |
FIG. 10

| WHOLE-LEAF PROCESSING | | | | | | | |
|---|---|---|---|---|---|---|---|
| LEAVES | pH | TOTAL SOLIDS (%) | MeOH SOLIDS | | | CALCIUM (mg/L) | MAGNESIUM (mg/L) |
| | | | TOTAL (%) | MALIC ACID (mg/L) | POLYSAC-CHARIDES (mg/L) | | |
| ALOE CORP | 3.65 | 1.151 (11510 mg/L) | 0.220 (2200 mg/L) | 2204 | 104 | 328 | 115 |
| ALOE LABS | 3.72 | 1.264 (12640 mg/L) | 0.224 (2440 mg/L) | 2038 | 402 | 332 | 93.3 |
| JAUMAVE | 3.65 | 2.520 (25200 mg/L) | 0.772 (7720 mg/L) | 2792 | 4928 | 628 | 110 |

FIG. 11

| TOTAL PROCESS WITHOUT PULP | | | | | | | |
|---|---|---|---|---|---|---|---|
| LEAVES | pH | TOTAL SOLIDS (%) | MeOH SOLIDS | | | CALCIUM (mg/L) | MAGNESIUM (mg/L) |
| | | | TOTAL (%) | MALIC ACID (mg/L) | POLYSAC-CHARIDES (mg/L) | | |
| ALOE CORP | 3.21 | 1.740 (17400 mg/L) | 0.320 (3200 mg/L) | 2204 | 996 | 285 | 144 |
| ALOE LABS | 3.11 | 1.809 (18090 mg/L) | 0.364 (3640 mg/L) | 2044 | 1596 | 296 | 119 |
| JAUMAVE | 3.65 | 4.254 (42540 mg/L) | 1.584 (15840 mg/L) | 8538 | 7302 | 681 | 496 |

FIG. 12

| TOTAL PROCESS WITH PULP | | | | | | | |
|---|---|---|---|---|---|---|---|
| LEAVES | pH | TOTAL SOLIDS (%) | MeOH SOLIDS | | | CALCIUM (mg/L) | MAGNESIUM (mg/L) |
| | | | TOTAL (%) | MALIC ACID (mg/L) | POLYSAC-CHARIDES (mg/L) | | |
| ALOE CORP | 3.67 | 1.166 (11660 mg/L) | 0.244 (2440 mg/L) | 1803 | 637 | 309 | 103 |
| ALOE LABS | 3.36 | 1.257 (12570 mg/L) | 0.399 (3990 mg/L) | 1803 | 3807 | 328 | 82 |
| JAUMAVE | 3.43 | 3.144 (31440 mg/L) | 0.968 (9680 mg/L) | 6054 | 3626 | 539 | 332 |

FIG. 13

METHOD OF PROCESSING ALOE LEAVES

BACKGROUND OF THE INVENTION

1. Field of the Invention

The present invention relates in general to a method for producing aloe products and in particular to a process for utilizing the waste residue from the hand-filleted process of aloe leaves to produce an aloe liquid that has calcium, magnesium, malic acid, and total solids in quantities that generally far exceed the parameters of quality established by the International Aloe Science Council.

2. Description of Related Art

The growing, preparation, and medicinal uses of the yellow sap of the aloe plant were known to the natives of the cape region of Africa long before it was made known to the European colonists and long before the early 1770's.

The aloe leaf consists of three layers. The first is the thick outer green rind. The second is a viscous, jelly-like mucilage layer into which vascular bundles, attached to the inner surface of the rind, protrude. The third is the fillet proper which has a structural integrity consisting of hexagonal structures containing the fillet fluid.

During the growth of the aloe plant, the materials of the mucilage layer, subsequent to their synthesis, are distributed to the storage cells (cellulose-reinforced hexagons) of the fillet, a process which is accompanied by dilution owing to the water which is stored in the fillet cells. The fillet consists of more than 99% water.

The pericyclic cells located at the top of the vascular bundles contain a yellow liquid called "yellow sap" or "latex". This material contains high concentrations of aloin and similar anthraquinones that exert a powerful laxative action when taken internally. Indeed, during the 18th to early 20th century, this yellow sap was collected and processed into a hard blackish material, the major product of the "laxative" trade era, while the rest of the leaf and its other constituents were discarded.

In order to avoid contaminating the internal fillet with the yellow sap, the traditional hand-filleting method of processing aloe leaves was developed. In this method, the lower one inch of the leaf base, the tapering point (2–4 inches) of the leaf top, and the short, sharp spines located along the leaf margins are removed by a sharp knife. The knife is then introduced into the mucilage layer below the green rind to avoid the vascular bundles and the top rind is removed. The bottom rind is similarly removed and the rind parts, to which a significant amount of mucilage remains attached, are discarded. Another portion of the mucilage layer is accumulated on top of the filleting table and is also discarded. As an additional procedure to limit inclusion of the inadvertent laxative anthraquinones, the fillets may be washed in water removing a majority of the deep layer of mucilage attached to the outer surface of the structurally integral fillet.

A second method of processing aloe leaves was developed using the whole leaf and is called the "whole leaf aloe process". In this process, the base, tip, and lateral spines of the aloe leaf are removed as previously stated leaving intact the thick outer green rinds. The leaf is then cut into sections and ground into a particulate slurry material. The slurry is then treated with special chemical products that break down the hexagonal structure of the fillet releasing the constituents. By means of a series of coarse screening filters or passage through a juice press, the rind particles are removed. The remaining juice is then passed through various filtering columns which remove the undesirable laxative agents. This process, performed properly, can produce a constituent-rich juice virtually free of the laxative anthraquinones. This process, developed in the 1980's is considerably less labor intensive and is more cost effective.

In this process, the large amount of water in the fillet in the leaf (50%+) is therefore processed and dilutes the valuable constituents in the aloe product.

In order to increase the desirable constituents of processed aloe in the final product, the elements in the product may be concentrated by (1) heat, (2) heat and vacuum, and (3) reverse osmosis.

Variously processed aloe juices can be reduced to powder form which improves shelf life compared to liquid products and eliminates the cost of shipping water.

In the spray-dried powder process, the liquid aloe is sprayed onto a matrix, usually high molecular weight maltodextrins, that usually constitute about 50% or more of the final product, using high heat. The high heat exposure changes to some degree some of the potentially beneficial constituents.

The lyophilized or freeze-dried powder utilizes cold (about −85° C.) and vacuum (usually about one-third atmosphere) which causes evaporation and sublimation of only the water. Heat-induced changes in the beneficial constituents are avoided but the process is considerably more expensive than the spray-dried process.

In the third process, fillets of aloe can be reduced to dehydrated pellets by placing them in a commercial-scale vegetable dehydrator operated at relatively low temperatures (slightly above body temperature) but for many hours. The dehydrated pellets are then ground to a fine powder.

The constituents that are most constant in the aloe plant and that are used as a standard by which to judge an aloe product are (1) total solids, (2) calcium, (3) magnesium, and (4) malic acid. The standard for calcium in the hand-filleted product is 241 milligrams per liter. The standard for magnesium in the hand-filleted product is 58.4 milligrams per liter. The standard for malic acid in the hand-filleted product is 2028 milligrams per liter. Finally, the standard for solids in the hand-filleted aloe product is 0.83 percent.

It has been known that the discarded residue from the filleting process that includes the rind contains a significant amount of mucilage that remains attached. It has been discovered that the highest concentration of potentially beneficial aloe constituents are found in this mucilage along with the rind as this layer represents the leaf constituents synthesized by the vascular bundle cells and powered by the energy developed in the green chlorophyll-containing rind cells through sun-induced photosynthesis.

It would be advantageous to make use of the discarded residue of the filleted process to have an aloe product that contains an enviably high concentration of desirable constituents that are virtually free of undesirable laxative anthraquinones. This novel process produces a product containing desirable constituents that may exceed those of aloe products subjected to concentration procedures intended to increase these desirable constituents.

SUMMARY OF THE INVENTION

In the present invention, the aloe leaves are hand-filleted by the traditional, old-fashioned, labor-intensive method. Instead of being discarded, the green rinds and the mucilage layer that are generated in the filleting process are utilized as part of the new process to provide the aloe product that has the high concentration of desirable constituents.

Thus the use of the discarded residue in the hand-filleted process in combination with a new process recovers the highest concentration of potentially beneficial aloe constituents found in the mucilage and the green rinds where the constituents are synthesized by the vascular bundle cells powered by energy developed in the green chlorophyll-containing rind cells through sun-induced photosynthesis.

Thus, it is an object of the present invention to provide an aloe slurry having a concentration of potentially beneficial aloe constituents that are usually many times higher than those same constituents in an aloe product formed by the normal filleted process and whole-leaf process using comparable leaves and are generally substantially higher than the average standards for an aloe product by the IASC (International Aloe Science Council) for certification.

It is still another object of the present invention to enable the enzymatic reaction between the cellulose-reinforced hexagons or storage cells and enzymatic-resistant constituents to be more completely digested thereby obtaining an aloe product having higher concentrations of the desired constituents.

Thus, the present invention relates to a process for generating an aloe product from aloe leaves comprising the steps of filleting each aloe leaf to obtain both a fillet and leaf residue, grinding only the leaf residue (rind portions and mucilage) into a slurry, and preparing an aloe product from the slurry.

The novel process also includes the steps of adding cellulase to the slurry to digest solids by an enzymatic action and continuously stirring the slurry with the cellulase for a period of time in the range of from about two to about four hours to obtain maximum digestion of the cellulase-reinforced hexagons in the slurry.

BRIEF DESCRIPTION OF THE DRAWINGS

These and other features of the present invention will be more fully disclosed when taken in conjunction with the following Detailed Description of the Preferred Embodiment(s) in which like numerals represent like elements and in which:

FIG. 7 is a generalized block diagram of the present inventive process;

FIG. 8 is a more detailed block diagram of the novel process of the present invention;

FIG. 9 is a block diagram of that part of the novel process of the present invention for separating the solids from the liquid;

FIG. 10 is a chart comparing the amounts of the most desired constituents of an aloe product formed by the prior art hand-filleted process from three different types of aloe leaves;

FIG. 11 is a chart comparing the amounts of the same important constituents in an aloe product formed by the prior art whole-leaf process from three comparable aloe leaves as in FIG. 10;

FIG. 12 is a chart comparing amounts of the important constituents in an aloe product formed using the process of the present invention from three comparable aloe leaves as illustrated in FIGS. 10 and 11 with no pulp in the final product; and FIG. 13 is a chart illustrating the comparison of the amounts of the important constituents in an aloe product formed according to the process of the present invention using three comparable aloe leafs as those used in the processes of FIGS. 10, 11, and 12.

DETAILED DESCRIPTION OF THE PREFERRED EMBODIMENT(S)

Figure 1:
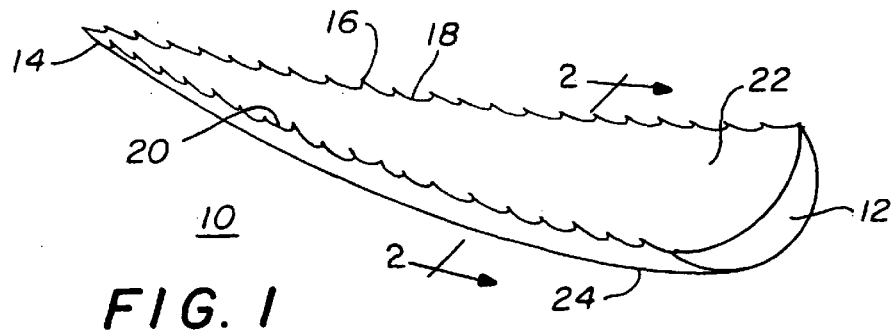
FIG. 1 is a perspective view of a typical aloe leaf.

A typical aloe leaf 10 is illustrated in FIG. 1. It includes a base 12, a tapering outer point 14 (the outer two to four inches of the leaf) short, sharp spines 16 located along the leaf margins 18 and 20, an outer thick green top rind 22 and bottom rind 24.

There are generally three known basic methods of processing aloe leaves. The first is the traditional hand-filleted aloe process. The second is the whole leaf aloe process, and the third involves powdered forms of aloe utilizing either spray-dried aloe powder, lyophilized aloe powder or dehydrated aloe powder.

Figure 2:
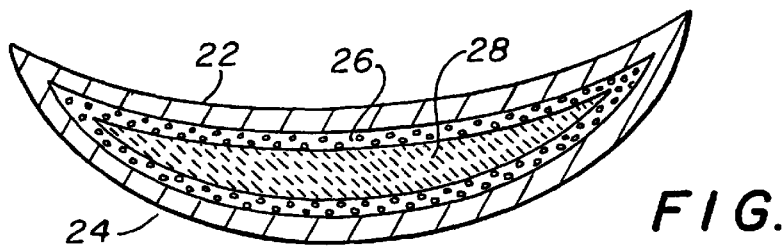
FIG. 2 is a generalized cross-sectional view of the aloe leaf taken along lines 2—2 of FIG. 1.

In order to better understand these processes, the physical structure of the aloe leaf should be understood. A cross section of the typical aloe leaf is illustrated in FIG. 2 wherein is shown the top thick green rind 22 and the bottom thick green rind 24. A layer 26 of viscous, jelly-like mucilage is immediately under the thick outer rinds 22 and 24. It is well known that this layer 26 has vascular bundles that are attached to the inner surface of the thick green rinds 22 and 24. These vascular bundles protrude into the mucilage layer. The fillet proper is designated by the numeral 28. It has structural integrity consisting of hexagonal structures containing the fillet fluid, which is 99% water.

It is also well known that pericyclic cells located at the top of the vascular bundles contain a yellow liquid called "yellow sap" or "latex". This material contains high concentrations of aloin and similar anthraquinones that exert a powerful laxative action when taken internally. Indeed, during the early 18th to 20th century, this yellow sap was collected and processed into a hard blackish material, the major product of the "laxative trade" era, while the rest of the leaf and its other constituents were discarded.

Thus in processing the aloe leaf, it is desirable to discard as much of the yellow sap as possible.

In the filleted process, in order to avoid contaminating the internal fillet with the yellow sap, the traditional hand-filleting method of processing aloe leaves was developed. In this well-known method, the lower one inch of the leaf base 12, the tapering point 14 (the two to four inches of leaf top), and the short sharp spines 16 located along the leaf margins 18 and 20 are removed by a sharp knife. The knife is then introduced into the mucilage layer 26 below the green rind avoiding the vascular bundles, and the top rind 22 is removed. The bottom rind is similarly removed and the rind parts, to which a significant amount of mucilage 26 remains attached are discarded. Thus, most of the "yellow sap" is discarded with the rind portions. However, another portion of the mucilage layer 26 is accumulated on top of the filleting table. As an additional procedure to limit the inadvertent laxative anthraquinones, the fillets 28 may be washed in water removing a majority of the deeper layer mucilage 26 attached to the outer surface of the structure of the integral fillet 28. The layer 26 of mucilage represents the constituents synthesized by the vascular bundle cells empowered by energy developed in the green chlorophyll-containing rind cells through sun-induced photosynthesis in a well-known manner. The materials of the mucilage layer 26, subsequent to their synthesis, are distributed to the storage cells of the fillet which are cellulose-reinforced hexagons. This process is accompanied by dilution owing to the water which is stored in the fillet cells. Water is the major fillet constituent and the fillet consists of more than 99% water.

Thus as can be readily appreciated, the hand-filleting method is very labor intensive. Owing to this fact, machines have been designed and employed in an attempt to simulate the hand-filleted techniques but generally the machine-generated product contains higher amounts of anthraquinone laxatives than the traditional hand-filleted approach.

The weighted distribution of aloe leaf fractions is as follows: average total weight 480 g, the base 30 g, rind components 170 g, and the residual fillet 280 g. Thus, about 51% of the aloe leaf is comprised by the fillet and 97% of it is water.

Figure 3:
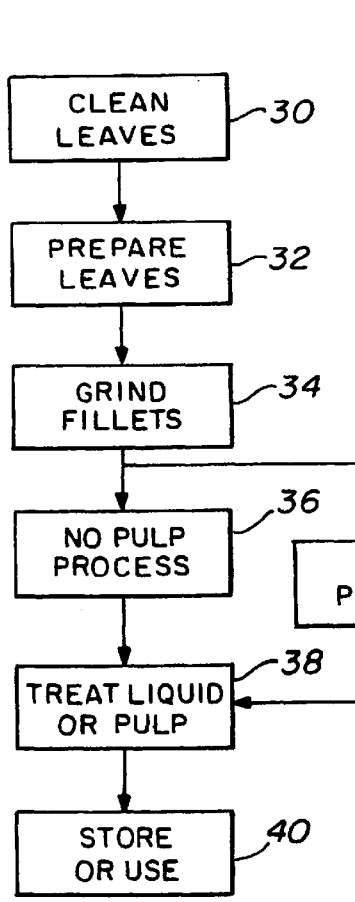
FIG. 3 is a generalized block diagram of the prior art process of preparing an aloe product using the hand-filleted method.

A generalized process diagram for the prior art hand-filleted method of producing an aloe product is illustrated in FIG. 3. At step 30, the aloe leaves are cleaned. At step 32, they are prepared by removing the rinds, the base, the tips, and the spiny edges. At step 34, the fillets are ground into a slurry. At step 36, if no pulp is desired, a process is provided to remove pulp. The remaining liquid is then treated at step 38. If the pulp process 37 is to be followed, the material from the slurry grinding process, including the pulp, is simply treated at step 38. At step 40, the prepared material is either stored or used in a particular manner well known in the art.

Figure 4:
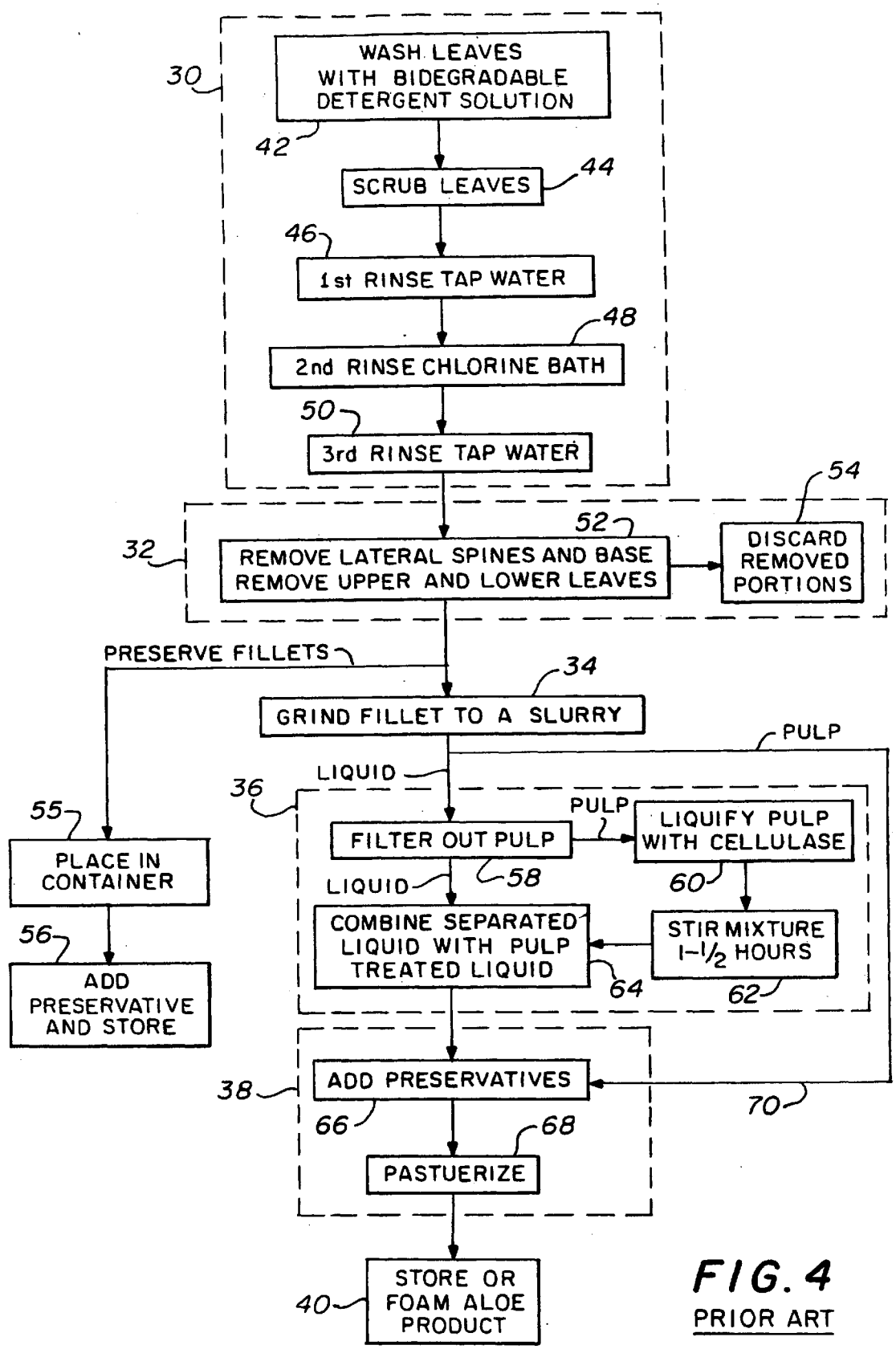
FIG. 4 is a detailed diagram of the hand-filleted process of FIG. 3.

Detailed method steps of the prior art hand-filleted process are illustrated in FIG. 4. Step 30, the step for cleaning the leaves illustrated in FIG. 3, includes the step 42 of washing the leaves with a biodegradable detergent solution where they commonly remain in solution for 15–20 minutes. They are then individually scrubbed at step 44 with stiff brushes to remove all residual soil, surface grime, and other adherent materials. The washed leaves are then placed in plastic baskets and transported to the rinsing stations 46, 48, and 50. Thus, in the leaf-rinsing procedure, the entire basket with its leaves are dipped sequentially in the following solutions as indicated. Rinse in clean tap water at step 46, rinse in a chlorine bath containing 50 ppm solution strength at step 48, and rinse again in clean tap water at step 50. The baskets and the leaf contents are then transported to the leaf trimming or leaf preparation stage 32.

At station 32, step 52, the base 12 of the leaf is removed (see FIG. 1) and the lateral spines 16 on lateral edges 18 and 20 are removed and the leaves again placed in the transport plastic baskets and transported to the fillet station. At the hand-filleted station, the upper and lower rinds 22 and 24 (see FIG. 2), the lateral outer edges 16,20, and the outer 2–4 inches of the tip or end 14 are removed using sharp knives and any microscopically visible defects in the fillet 10 are cut away and discarded at step 54. Filleting procedures take place on the top surface of stainless steel tables. The intact fillets are routed to the end of the filleting table and placed in stainless steel containers holding approximately 100 liters (95 k).

If preserved fillets are being prepared, the fillets are placed in the containers at step 55 and then transferred to a drum area for preservation procedures 56. To preserve the fillets, each sanitized drum is fitted with a plastic liner and is filled to one-third capacity with a solution containing 104 g of sodium benzoate and 650 g of citric acid in one gallon of aqueous solution as a preservative. The fillets are transferred by hand from the stainless steel transport tank to the preservative-containing drum making certain that the fillet is bathed by the preservative solution. When the drum is one-third full, a second gallon of the preservative solution is placed in the drum and the fillet transfer accomplished as set forth previously. Lastly, a third gallon of the preservative solution is placed in the drum and the fillets placed therein. When the drum is full, the plastic liner is secured using strong rubber bands sealing the fillets in the preservative solution.

If the fillets are to be converted into aloe juice, the stainless steel tank containers are transported to the grinding machine at step 34 wherein the fillets are forced through stainless steel mesh approximating 1 cm orifices.

If hand-filleted aloe juice without pulp is desired, the following steps are taken. The aloe material from the post-grinding stainless steel holding tank is filtered at step 58 to remove the pulp and leave a liquid. The removed pulp is then treated at step 60 with cellulase 4000 (230 g per standard batch) at ambient temperature while constantly stirring for one and one-half hours at step 62. The cellulase 4000 enzymatically digests some of the solids, such as the hexagonal cells that hold the fillet together, to form aloe liquid. The resulting aloe liquid from step 62 is combined at step 64 with the filtered aloe liquid from the filter step 58.

At general step 38, preservatives are added at step 66 and the product is pasteurized at step 68. At step 66, the preservative mixture has a final concentration of 0.1% sodium benzoate, the maximum amount allowed by the FDA, and 0.05% potassium sorbate. The sodium benzoate deters bacteria from developing while the potassium sorbate deters yeast and mold from occurring. As the aloe mixture is treated, admixture with the preservatives is assured by constant stirring. The pH of the aloe material is then adjusted to a range of 3.0–3.5 using citric, phosphoric, or ascorbic acid. The aloe material is then subjected to further continual stirring for an additional 5–10 minutes.

At step 68, the aloe material is pasteurized by raising the temperature to 170° F., which is usually accomplished in 45–60 minutes. On obtaining the desired temperature, the material is held at that point for 30 minutes. Thereupon the material is transferred to 55 gallon drums. The drums, of course, are sanitized in a well-known manner.

As stated earlier, the hand-filleted process of the aloe leaf is old and well known in the art. The important things to note about this process is that (1) the removed outer green rind 22, 24 (FIG. 1), the lateral edges 18, 20 with the spine 16, and the outer tip 14 are discarded, and (2) most of the yellow sap has been removed with discarded refuse. Thus, there is no need for cellulase to be added for enzymatic action and there is no need to treat the slurry to remove the yellow sap.

The second process that is well known in the art is the whole-leaf process. This process is illustrated in the flow-chart of FIG. 5.

At step 72, the leaves are once again cleaned as they were in step 30 in FIG. 4 for the hand-filleted process.

At step 74, the whole leaf is prepared for the grinding station in step 76. At step 78, the slurry produced by the grinding process at step 76 is separated into a liquid and solid. The solids are discarded at step 80 and the liquid treated at step 82. At step 84, the liquid is stored or is used to prepare an aloe product.

Figure 6:
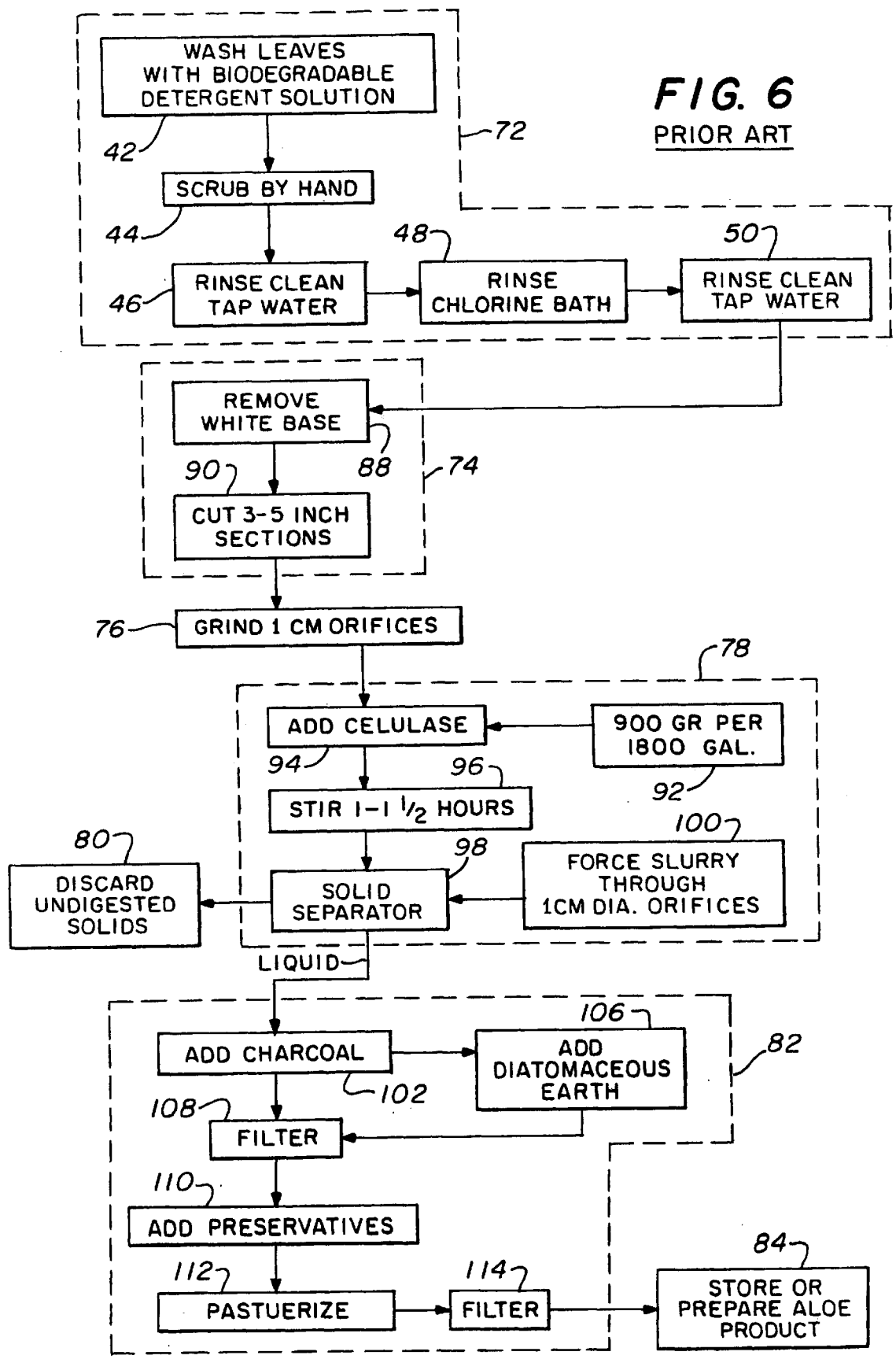
FIG. 6 is a detailed block diagram of the whole-leaf process of preparing an aloe product.

The details of the whole-leaf process are disclosed in FIG. 6.

Figure 5:
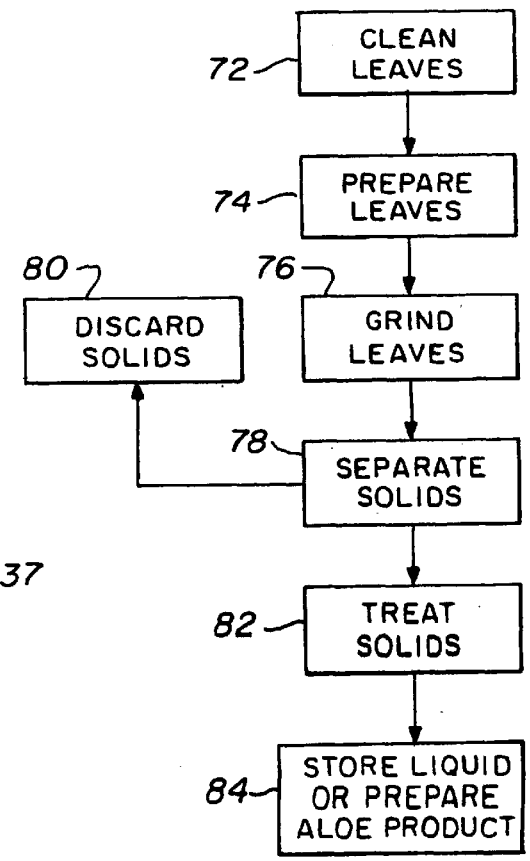
FIG. 5 is a generalized block diagram of the whole-leaf process for preparing an aloe product.

The leaf-cleaning process 72, shown in FIG. 5, is illustrated in detail in FIG. 6 and shows that the leaves are washed with a detergent at step 42, scrubbed by hand at step 44, rinsed with clean tap water at step 46, rinsed in a chlorine bath at step 48, and rinsed a third time in clean tap water at step 50. These steps are the same the steps shown in FIG. 4 for the hand-filleted process.

The leaf preparation step 74 is somewhat different in the whole-leaf process. There, in contradistinction to the hand-filleted process, only the white base 12 of the leaf is removed at step 88. The lateral spines 16 and the leaf tip 14 (FIG. 1) remain in situ. The debased entire leaves are then cut into 3–5 inch sections at step 90 and these portions are transferred to the grinding station 76.

During the grinding step 76, the cut leaf sections are forced through stainless steel mesh approximating 1 cm orifices. From the grinder, the material is pumped into a holding tank completely isolated from the ambient environment by stainless steel lids. The ground slurry from the grinding operation at step 76 must then have the solids separated from the liquid at step 78. At step 92, 900 g of cellulase 4000 per 1800 gallons of slurry are mixed at step 94. The cellulase 4000 digests some of the solids through an enzymatic process that is well known in the art. This mixture of cellulase with the aloe leaf puree is assured by the constant stirring maintained by 1½ hours at step 96. The actual time interval of the cellulase enzymatic reaction is determined by changes in liquidity of the solution owing to the fact that the reaction takes place at somewhat differing rates depending upon the ambient temperature. Forty-five minutes to one and one-half hours are deemed sufficient time.

After the appropriate degree of liquidity is obtained, which is defined in terms of reduction of viscosity of 5000 centipoise (cP) or less, the solution is passed through a finisher or solid separator at step 98 which separates the undigested solids from the solution. The undigested solids are discarded at step 80. The separation occurs because the slurry is forced through 1 cm diameter orifices at step 100.

The juice from the solid separator or finisher at step 98 must be treated to remove undesirable components such as the laxative elements. Further, other undesirable components of laxative elements may be also removed. Thus, at step 102, charcoal in the amount of 22–35 kg per 500 gallon tank is added to the liquid and is treated for 1½ hours. The charcoal removes undesirable components such as the laxatives. The charcoal and juice are continuously stirred throughout the charcoal treatment.

After the above treatment, at step 106, diatomaceous earth, in an amount equivalent to the amount of charcoal used, is added to the charcoal juice admixture and an additional time period of 45–60 minutes, with constant stirring, is allowed.

The material, comprising aloe juice, charcoal, and diatomaceous earth, is then circulated through a charcoal filter utilizing one micron interstage filter paper at step 108 until the effluent is crystal clear. The term "crystal clear" is a term well known in chemistry and is defined as "a complete or total absence of". The filtering process is normally accomplished in 20–25 minutes.

The clear juice is then pumped through stainless steel tubing to a container at step 110 where the preservative mixture is added. Again, it is 0.1 sodium benzoate and 0.05% potassium sorbate. As the clear aloe juice is transferred from the filter 108 to step 110 for adding preservatives, constant stirring of the liquid is provided to assure admixture with the preservatives.

The pH of the aloe material is again adjusted to the 3.0–3.5 range using citric, phosphoric, or ascorbic acid. Then the aloe material is further subjected to continued stirring for an additional 5–10 minutes.

At step 112, the aloe juice is pasteurized by raising the temperature to 170° F., which is usually accomplished in 45–60 minutes. Upon obtaining the desired temperature, the material is held at that point for 30 minutes. Thereupon the material is transferred to step 84 for storage in sanitized drums or for use in preparing an aloe product.

The preserved and pasturized material from step 112 is normally passed through a filter 114 that is a sterile 5–10 micron filter immediately prior to being placed in sanitized drums for storage at step 84. For some applications, the material is filtered through 0.2 micron filters, essentially removing all microorganisms and infectious particles.

Note in this "whole-leaf" process that the fillet 28 is ground up with the remaining portions of the leaf. This means that the fillet, about 51% of the leaf, has water therein (99%) that dilutes significantly, the aloe juice formed. Further note that the enzymatic action of the cellulase 4000 to digest the solids into liquids takes place over a period of time of from 45 minutes to 1–1½ hours.

The novel process of the present invention is illustrated generally in FIG. 7. At step 116, the leaves are processed into fillets and a refuse as done in the filleted process described previously. At step 118, only the refuse, or removed aloe leaf portions, is ground into a slurry and, at step 120, the slurry is processed into an aloe product. One significant distinction between the process illustrated in FIG. 7 and the whole-leaf process or the hand-filleted process is that in the hand-filleted process the refuse (or removed leaf portions) is discarded as previously shown at step 54 in FIG. 4. In the whole-leaf process, the entire leaf is processed thus including the fillet that is 99% water and that significantly dilutes the finished product.

FIG. 8 is a more detailed flowchart of the steps illustrated in FIG. 7. At step 116, the leaves are cleansed at step 122 according to the same process used by the hand-filleted or whole-leaf process. At step 124, the leaves are filleted as described previously in relation to the hand-filleted process but the fillets are used at step 126 for some purpose such as described earlier in relation to the hand-filleted process described earlier.

It is the refuse, or discarded leaf portions, from the filleting process that is ground at step 118 and processed. In the process step 120, at step 127, the solids are separated from the liquid as shown at step 128. The liquid is coupled to step 130 where it is treated.

If a process with pulp is desired, then the separating step 127 of separating solids is omitted and the slurry output from the grinding step 118 is coupled directly to the treatment stage 130.

The details of the novel process step 20 are illustrated in FIG. 9. In FIG. 9, at step 118, again it is the refuse, or discarded leaf portions, that is ground to a slurry. Again, it is to be noted that this process differs from the hand-filleted process and the whole-leaf process in that in the hand-filleted process the refuse is discarded, while in the whole-leaf process the refuse is combined with the fillet and the fillet, being 99% water and over half of the aloe leaf, significantly dilutes the resulting product.

Thus, the ground refuse or slurry from step 118 is coupled to the solid separating process step 120 where, at step 136, cellulase 4000 is added again at 900 g per 1000 gallons of fluid as shown at step 138. The addition of cellulase is, again, to digest solids in the refuse in an enzymatic process. It was advantageously discovered that a higher concentration of beneficial aloe constituents can be obtained by allowing a greater length of time for enzymatic action to occur. Therefore, this admixture is continually stirred from 2–4 hours at step 140. This is considerably different from the whole-leaf process in that the whole-leaf process is continually stirred for 45 minutes to 1–1½ hours. Since the novel inventive process is dealing with the outer rind and the tip of the aloe plant with the significant amount of mucilage remaining attached, it was found that by stirring the mixture from 2–4 hours at step 140, the maximum solid reduction to the liquid containing the beneficial constituents can occur most efficiently.

At step 142, the solids separator forces the slurry through 1-centimeter orifices at step 144 and undigested solids at step 128 are taken out of the mixture. The remaining fluid is transferred to step 130 for treatment as described previously in relation to the whole-leaf process to remove the undesirable components such as laxative and the like.

Thus, it can be seen that the novel process includes two major elements that are significantly different from the prior art processes. First, when the leaves are hand-filleted, as described earlier in relation to the hand-filleted process, the refuse, the outer thick green rind, top and bottom layers, the outer 2–4 inches of the leaf top and the viscous, jelly-like mucilage layer attached to the inner surface of the outer thick green rind, are the only elements of the aloe leaf used in the present process. In the whole-leaf process, the entire leaf including the fillet is used, while in the hand-filleted process, the refuse is discarded and only the fillet is used. The present process utilizes only the waste or refuse from the hand-filleted process.

Second, when the cellulase is added to enzymatically digest solids, it has been found that if it is continuously stirred from 2–4 hours that the maximum amount of the beneficial aloe constituents is recovered most efficiently. It will be recalled that the highest concentration of potentially beneficial aloe constituents is found in the mucilage as this layer represents the constituents synthesized by the vascular bundle cells during the sun-induced photosynthesis process.

FIGS. 10, 11, 12, and 13 are comparisons of three different types of leaves for the three different types of processes. Thus, in FIG. 10, using the hand-filleted process, the beneficial constituents obtained with first and second leaves from the lower valleys in Texas and the Jaumave leaf from Mexico are compared. FIG. 11 compares the constituent elements in aloe product developed from three comparable leaves using the whole-leaf process. FIG. 12 compares the constituent elements in the aloe product formed from three comparable leaves using the present inventive process without pulp. Finally, FIG. 13 compares the processing of three comparable leaves with the present inventive process where the aloe product contains pulp.

It should be explained that the constituent elements in the aloe leaves vary widely according to a number of factors including the weather during the time the plant was growing, the temperature, the soil conditions, the wind conditions, the amount of sunlight, and the like. Because of these factors, the International Aloe Science Council has established ranges of standards and an average for the important constituent elements of the aloe leaf. For instance, for the whole leaf aloe vera gel, the product should contain the following:

| TEST | SPECIFICATION | AVERAGE |
|---|---|---|
| pH | 3.5–4.7 | 3.9 |
| Solids (%) | 0.95–2.0% | 1.2% |
| Calcium (mg/L) | 444.8–1020 mg/L | 565.1 mg/L |
| Magnesium (mg/L) | 33–230 mg/L | 82 mg/L |
| Malic Acid (mg/L) | 2780–10,670 mg/L | 4287 mg/L |

Note that no standard currently exists for polysaccharides. They are, however, very important because they are considered, in the literature, to be among the most important biologically active constituents.

It should be noted, however, that the charts shown in FIGS. 10–13 simply compare, in each case, three comparable leaves from three different areas with a particular process. For instance, in FIG. 10, the hand-filleted process has been used on three different leaves, the Aloe Corp. leaf, the Aloe Labs. leaf, and the Jaumave leaf. These three leaves are raised in different areas, the first two in southern Texas and the third in Mexico. Note that the important constituent elements are total solids, malic acid, calcium, and magnesium and, as stated above, polysaccharides. Notice that in the results of the hand-filleted process shown in FIG. 10, the Jaumave leaf produces a product that is substantially improved over the other two leaves. For instance, the malic acid in the product produced from the Jaumave leaf is approximately 10% higher than the malic acid in the Aloe Corp. leaf product and 12% higher than the malic acid content in the product produced from Aloe Labs. leaves. The polysaccharides in the Jaumave leaf are 3 to 9 times greater than in the other two leafs. The calcium is 2 to 4 times as much, and the magnesium is about twice as much as each of the other two leaves. Apparently from this test it can be concluded that the Jaumave leaf is raised under conditions such that the leaf has higher quantities of the desired constituents in the fillets.

The resulting product constituents using the whole-leaf process are compared as illustrated in FIG. 11. Note that the total solids in the Jaumave leaf are at least twice as much as either of the other two leaves. Further, the malic acid constituent is at least a third more in the Jaumave leaf product and the polysaccharides are as much as fifty times the polysaccharides in the Aloe Corp. leaf and twelve times as much as the polysaccharides in the Aloe Labs. leaf. The calcium is almost twice as much in the product formed from the Jaumave leaf when compared to the calcium in the product formed by the other leafs, all three leaves being processed using the whole-leaf process. The magnesium is approximately the same.

Now, compare the constituent elements in the product formed from all three types of leaves using the process of the present invention without pulp. Note, that the total methanol precipitable solids, MeOH solids, increase dramatically in the product formed by all three leaves using the present inventive process. The MeOH total solids from the two valley leaves, Aloe Corp. and Aloe Labs., more than double, while those solids in the Jaumave leaf increase about five times. The malic acid in the Aloe Corp. leaf derived with the present inventive process is 60% higher than the malic acid in the same leaves in the hand-filleted process and approximately 70% higher than the malic acid derived from the product formed from the Aloe Labs. leaf using the hand-filleted process. The Jaumave leaf malic acid derived with the novel inventive process is six times higher than the malic acid obtained from a comparable Jaumave leaf processed by the hand-filleted method and is three times higher than the amount of malic acid obtained from a comparable leaf processed by the whole-leaf process.

The polysaccharides for the Aloe Corp. aloe leaf obtained with the present inventive process is five times higher than the quantity of polysaccharides obtained with a comparable leaf using the hand-filleted process. It is also ten times higher than the polysaccharides obtained from a comparable Aloe Corp. leaf using the whole-leaf process. See FIG. 11 for the whole-leaf process results.

Using the same comparisons with the Aloe Labs. leaf, the present inventive process derives polysaccharides that are three times the amount obtained with a comparable leaf using the hand-filleted process and four times the amount using the whole-leaf process. The novel process also generates 3½ times more polysaccharides than generated from a comparable Jaumave leaf using the hand-filleted process and 50% more polysaccharides than was obtained from a comparable Jaumave leaf using the whole-leaf process. The same thing occurs with respect to the calcium and the magnesium. One exception with the magnesium is that it is only about 20% higher for the two valley leafs and approximately five times higher using the Jaumave leaf and the whole-leaf process.

FIG. 13 discloses the same three leaves and their important constituents that are obtained using the present inventive process with pulp. It can be seen that the malic acid for all three leaves is much higher than the malic acid for the corresponding leaves utilizing the hand-filleted process. Only the Jaumave leaf generates greater malic acid with the normal process. The malic acid amount is more than twice that for a comparable leaf using the whole-leaf process. The amount of polysaccharides obtained from all three comparable aloe leaves with the present inventive process having pulp in it is considerably higher than the polysaccharides obtained with the three leafs utilizing the hand-filleted process. The polysaccharides are also higher for the Aloe Corp. leaf and the Aloe Labs. leaf than the corresponding leaves in the whole-leaf process.

However, the amount of polysaccharides for the Jaumave leaf of the present process with pulp is approximately one-third less than the polysaccharides obtained with the whole-leaf process. The reason for this disparity is related to the time of harvest of the aloe leaf. $CO_2$ taken into the plant at night when the stemata (pores) are open, is stored as malic acid. The malic acid with sunlight generated photosynthetic energy, converts the malic acid into the polysaccharides. If harvested and processed early in the morning, the plant has not had time to convert the malic acid to polysaccharides.

The calcium is essentially the same in all three leaves when compared with the whole-leaf process and the magnesium is the same as the first two leaves in the whole-leaf process but is three times higher than the comparable Jaumave leaf used in the whole-leaf process.

Thus, in these charts it can be seen that regardless of the wide variation in elements in the aloe leaves, that the present inventive process, no matter which leaf was used in the comparisons, achieves substantially better results than the other known processes of hand-filleting and whole-leaf processing. Because the products made from the aloe liquid obtained by the present process, either with or without pulp, is so high in the important constituents of total solids, malic acid, polysaccharides, calcium, and magnesium that it is a substantially improved product obtained with the new process.

Thus, there has been disclosed a new process for producing an aloe product from aloe leaves which is distinguished from the prior art methods of hand-filleting and whole-leaf processing by not using the fillet at all but only using the residue from the hand-filleted method and processing it. Further, when the liquid is being separated into liquids and solids, the enzymatic digestion of hexagonal solids by the use of cellulase to obtain the important constituents is improved by continuously stirring the mixture containing the cellulase for a period in the range of from about 2 to about 4 hours to allow maximum digestion of the solids by the cellulase in the most efficient time period.

The corresponding structures, materials, acts, and equivalents of all means or step plus function elements in the claims below are intended to include any structure, material, or act for performing the function in combination with other claimed elements as specifically claimed.

What is claimed is:

1. A process for generating an aloe product from aloe leaves having an internal fillet comprising the steps of:
   filleting each aloe leaf to remove the internal fillet and leave a leaf residue;
   grinding only the leaf residue into a slurry; and
   preparing an aloe product from the slurry.

2. The process of claim 1 wherein filleting the aloe leaves to remove the internal fillet therefrom is hand-filleting.

3. The process of claim 1 further comprising the steps of:
   cleansing the aloe leaf before filleting it;
   and wherein the preparing comprises the steps of:
   separating the slurry formed into a liquid and solids; and
   treating the separated liquid to remove laxatives before forming said aloe product.

4. The process of claim 3 further comprising the step of adding preservatives to the treated separated liquid to maintain polysaccharides and organic acids in said treated liquid.

5. The process of claim 4 further comprising the step of pasteurizing the treated separated liquid containing said preservatives to increase the shelf life of said aloe product.

6. The process of claim 3 wherein the step of treating the separated liquid to remove laxatives further comprises the steps of:
   adding charcoal in sufficient amounts to remove a portion of said laxatives from said treated separated liquid; and
   adding diatomaceous earth in amounts substantially equal to the added charcoal to substantially remove the remaining laxatives in said liquid.

7. The process of claim 6 further comprising the step of filtering the treated separated liquid to obtain a crystal clear effluent from which said aloe product is formed.

8. The process of claim 3 wherein the step of separating the slurry into a liquid and solids further comprises the steps of:
   adding cellulase to said slurry to digest solids by an enzymatic action; and
   continuously stirring said slurry with said cellulase for a period of time in the range of from about 2 to about 4 hours.

9. The process of claim 8 further comprising the step of digesting cellulose reinforced hexagons in said slurry with said cellulase by said continuous stirring from about 2 to about 4 hours.

10. The process of claim 1 wherein the step of grinding only said leaf residue to form a slurry further comprises the step of forcing the ground slurry through orifices having a diameter of approximately one centimeter to remove solids from said slurry.

11. The aloe product formed by the process of claim 1.

12. A process for generating a liquid from aloe leaves having an internal fillet comprising the steps of:
   cleansing each aloe leaf;
   filleting each aloe leaf to remove the internal fillet and leave a leaf residue;
   grinding only the leaf residue into a slurry;
   separating the slurry formed into a liquid and solids; and
   treating the separated liquid to remove laxatives to form said liquid.

13. The liquid formed by the process of claim 12.

* * * * *